United States Patent [19]

Franke

[11] Patent Number: 4,628,086
[45] Date of Patent: Dec. 9, 1986

[54] PREPARATION OF DIOXAZINE COMPOUNDS

[75] Inventor: Günter Franke, Leichlingen, Fed. Rep. of Germany

[73] Assignee: Bayer Aktiengesellschaft, Leverkusen, Fed. Rep. of Germany

[21] Appl. No.: 803,457

[22] Filed: Dec. 2, 1985

[30] Foreign Application Priority Data

Dec. 8, 1984 [DE] Fed. Rep. of Germany ....... 3444888

[51] Int. Cl.[4] ................... C07D 265/34; C07D 279/14
[52] U.S. Cl. ...................................... 544/31; 544/74; 544/75; 544/76; 544/77
[58] Field of Search ....................... 544/31, 74, 75, 76, 544/77

[56] References Cited

U.S. PATENT DOCUMENTS 4,532,323 7/1985 Jäger ................................... 544/77

Primary Examiner—Richard L. Raymond
Attorney, Agent, or Firm—Sprung, Horn, Kramer & Woods

[57] ABSTRACT

A process for the preparation of dioxazine compounds of the formula

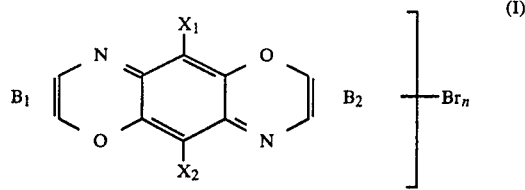

in which
B₁ and B₂ designate a ring system with 1, 2, 3 or 4 carbocyclic and/or heterocyclic rings which can be substituted, and
$X_1$ and $X_2$ designate hydrogen, halogen, —R', —OR', —NHR', —NR'R",

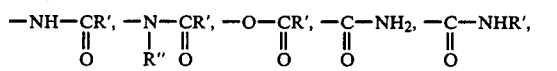

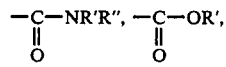

R' and R" representing alkyl, cycloalkyl, aryl and aralkyl and
n denoting 2, 3, 4, 5, 6, 7, 8, 9, 10 or 11, it being possible for the n bromine atoms, independently of one another, to replace both H atoms of the ring systems B₁ and B₂ or their substituents and H atoms of $X_1$ and $X_2$ as well as $X_1$ and $X_2$ themselves,
is characterized in that compounds of the formula II

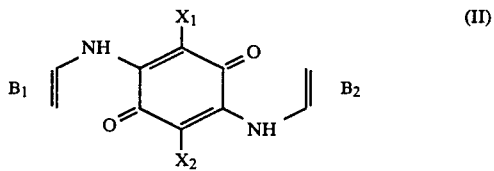

are reacted with bromine, preferably in the presence of diluents.

13 Claims, No Drawings

PREPARATION OF DIOXAZINE COMPOUNDS

The invention relates to a process for the preparation of dioxazine compounds of the formula $$\left[ B_1 \underset{O}{\overset{N}{\bigcirc}} \underset{X_2}{\overset{X_1}{\bigcirc}} \underset{N}{\overset{O}{\bigcirc}} B_2 \right] - Br_n \quad (I)$$

in which
B$_1$ and B$_2$ designate a ring system with 1, 2, 3 or 4 carbocyclic and/or heterocyclic rings which can be substituted, and
X$_1$ and X$_2$ designate hydrogen, halogen, —R′, —OR′, —NHR′, —NR′R″, $$-NH-\underset{\underset{O}{\parallel}}{C}-R',\ -\underset{R''}{N}-\underset{\underset{O}{\parallel}}{C}R',\ -O-\underset{\underset{O}{\parallel}}{C}R',\ -\underset{\underset{O}{\parallel}}{C}-NH_2,\ -\underset{\underset{O}{\parallel}}{C}-NHR',$$

$$-\underset{\underset{O}{\parallel}}{C}-NR'R'',\ -\underset{\underset{O}{\parallel}}{C}-OR',$$

R′ and R″ representing alkyl, cycloalkyl, aryl and aralkyl and
n denoting 2, 3, 4, 5, 6, 7, 8, 9, 10 or 11, it being possible for the n bromine atoms, independently of one another, to replace both H atoms of the ring systems B$_1$ and B$_2$ or their substituents and H atoms of X$_1$ and X$_2$ as well as X$_1$ and X$_2$ themselves, which is characterized in that compounds of the formula (II)

$$B_1 \underset{O}{\overset{NH}{\bigcirc}} \underset{X_2}{\overset{X_1}{\bigcirc}} \underset{NH}{\overset{O}{\bigcirc}} B_2 \quad (II)$$

are reacted with bromine, preferably in the presence of diluents.

In exceptional cases, the oxidation products of the compounds of the formula (I) are formed in the process according to the invention. In the case where (II) contains substituents X$_1$ and X$_2$ which, in the reaction according to the invention, are at least partially exchanged for bromine, the reaction of (II) leads, for example, in the case of X$_1$=X$_2$, to compounds of the formula (III)

$$\left[ B_1 \underset{O}{\overset{N}{\bigcirc}} \underset{Br_m}{\overset{Y_{2-m}}{\bigcirc}} \underset{N}{\overset{O}{\bigcirc}} B_2 \right] - Br_{n-m} \quad (III)$$

in which

Y designates one of the substituents mentioned for X$_1$ and X$_2$, which can be exchanged for bromine in the process according to the invention, such as chlorine or hydrogen, and
n has the meaning given above, the condition $0 < m \leq 2$ applying for m.

Possible substituents of the ring systems B$_1$ and B$_2$ are preferably halogen, —R′, —OR′, —NHR′, —NR′R″, $$-NH-\underset{\underset{O}{\parallel}}{C}-R',\ -\underset{R''}{N}-\underset{\underset{O}{\parallel}}{C}R',\ -O-\underset{\underset{O}{\parallel}}{C}R',\ -\underset{\underset{O}{\parallel}}{C}NH_2,\ -\underset{\underset{O}{\parallel}}{C}-NHR',$$

$$-\underset{\underset{O}{\parallel}}{C}-NR'R'',\ -\underset{\underset{O}{\parallel}}{C}-OR',\ -OH,\ -SR',\ -CN,\ -SCN,$$

$$-NO_2,\ -NH_2,\ -R'-O-R'',\ R'\underset{\underset{O}{\parallel}}{C}-$$

and R′SO$_2$—
R′ and R″ having the meanings given above.

The ring systems B$_1$ and B$_2$ consist preferably of 2, 3 or 4 fused aromatic 5-membered and 6-membered rings which can contain hetero-atoms such as N, O and S.

In the examples which follow, the positions marked x indicate the bond with oxygen, formed on cyclization; the positions marked y indicate the bond with N:

-continued

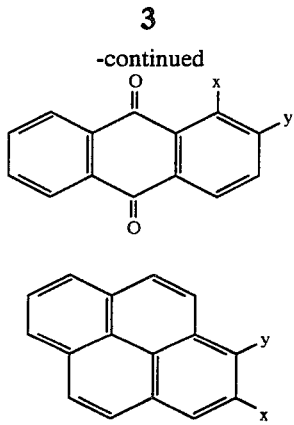

in which
$R_1$ designates hydrogen, $R_2$—, —$R_2$—O—$R_3$—,

or $R_2$—$SO_2$—,
$R_2$ and $R_3$ designating alkyl, cycloalkyl, aryl and aralkyl.

In connection with formula (I), halogen preferably represents chlorine and bromine, alkyl preferably represents $C_1$-$C_4$-alkyl, cycloalkyl preferably represents cyclopentyl and cyclohexyl, aryl preferably represents phenyl and p-tolyl, and aralkyl preferably represents benzyl and phenylethyl.

The process according to the invention is advantageously carried out in high-boiling solvents, which are inert under the reaction conditions, for example nitrobenzene or chlorinated hydrocarbons such as pentachloropropane, o-dichlorobenzene or trichlorobenzene, at 10°-270° C. preferably at 130°-250° C. and especially at 170°-220° C., if appropriate under pressure and if appropriate in an inert gas atmosphere. The reaction can also be carried out directly in bromine.

The precursors (II) are prepared, for example, by condensing amino compounds of the formulae (Iva) and (Ivb) with quinones of the formula (V), in accordance with the equation given below:

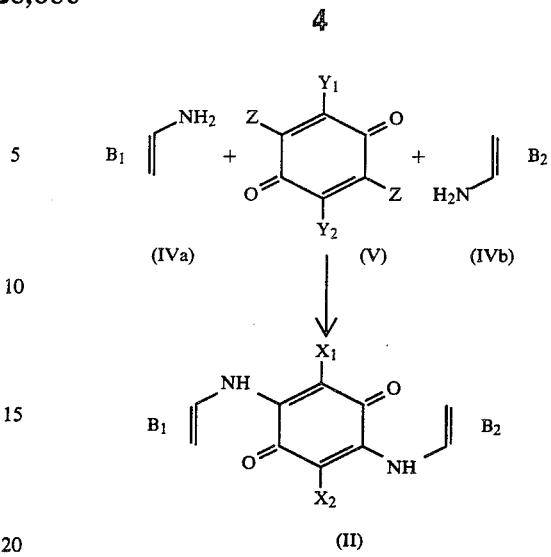

Z preferably designates halogen, in particular chlorine, hydroxyl, alkoxy and aryloxy, in particular phenoxy.

Examples of "central components" of the formula (V) are compounds of the formulae (VI) and (VII)

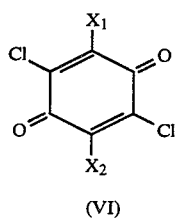 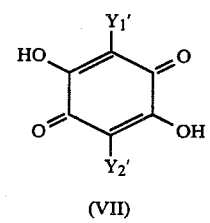

in which
$Y_1'$ and $Y_2'$ have the same meaning as $X_1$ and $X_2$ but with the exception of halogen.

It is advantageous, whenever possible, to perform the preparation of (II) and the subsequent conversion to the pigment (I) without intermediate isolation of (II).

If, of the precursors of the formula (II), those of the formula (VIII) are employed in the reaction according to the invention, secondary products of the formula (IX) are obtained in some cases in place of the corresponding dioxazines by further oxidation of the latter according to the following equation:

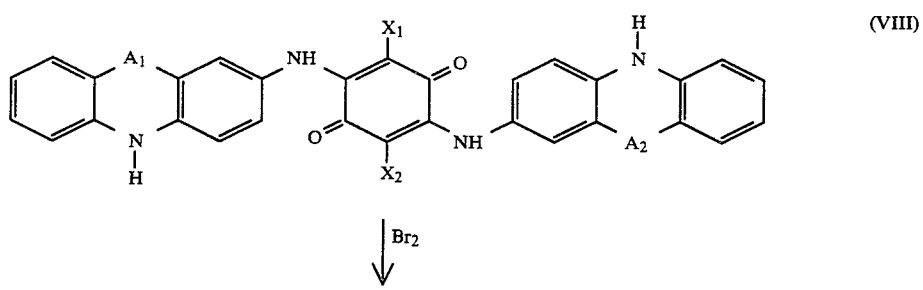

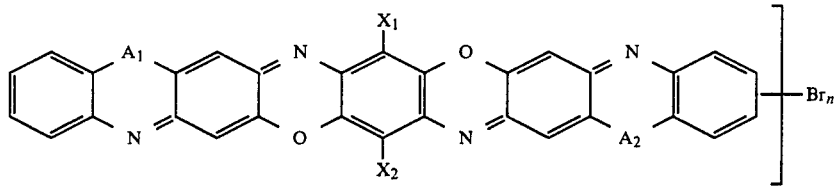

In this equation, $A_1$ and $A_2$ independently of one another denote a direct bond or a hetero-atom such as O, S or $NR_1$. The compounds (VIII) and (IX) can also carry fused benzene rings. The compounds of the formula (IX) also represent valuable pigments.

Among the precursors of the formula (II) those of the formula (X) should be mentioned as particularly suitable for the process according to the invention

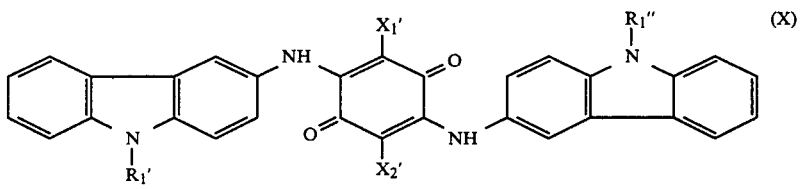

in which $X_1'$ and $X_2'$ have the same meaning as $X_1$ and $X_2$, and
$R_1'$ and $R_1''$ independently of one another have the meaning or $R_1$.

In the preferred compounds (X), $X_1'$ and $X_2'$ and also $R_1'$ and $R_1''$ are identical.

Among the compounds (X) preferred for the process according to the invention, those should be mentioned in particular, wherein:

$X_1'$ and $X_2'$ = hydrogen or chlorine
$R_1'$ and $R_1''$ = $C_1$-$C_4$-alkyl, preferably ethyl.

When the reaction according to the invention is carried out with the compounds of the formula (X), which are particularly suitable for this purpose, those procedures are to be singled out, as regards the quantity of bromine, which lead to compounds of the formula (XI)

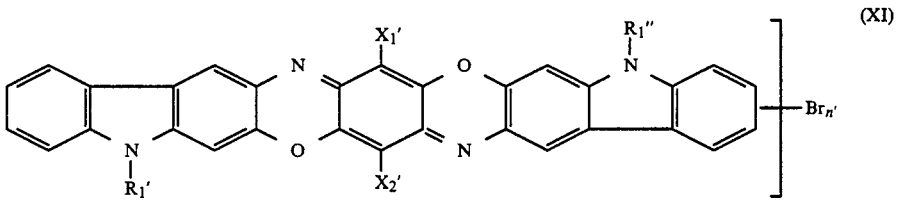

in which
$n' = 4, 5, 6, 7$ or $8$,
$R_1'$ and $R_1''$ and also $X_1'$ and $X_2'$ having the meanings given above.

Because, for the case of $X_1' = X_2' =$ hydrogen or chlorine, a part of $X_1'$ and $X_2'$ is always exchanged for bromine in the reaction according to the invention, the compounds of the formula (XI) can also be represented by formula (XII)

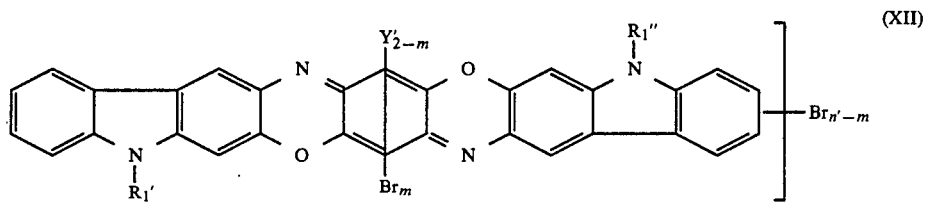

wherein
$Y' =$ hydrogen or chlorine,
$0 < m \leq 2$, $R_1'$, $R_1''$ and $n'$ having the meanings given above.

The compounds of the formula (I), obtained by the process according to the invention, are suitable, preferably after conventional dry or wet conditioning, for the most diverse pigment applications, due to their good pigment properties. Thus, they can be used for the preparation of pigmented systems of very high fastness, such as mixtures with other materials, preparations, paints, printing inks, coloured paper and coloured macromolecular materials. Mixtures with other materials can be understood, for example, as those with inorganic white pigments such as titanium dioxide (rutile). Examples of preparations are flush pastes with organic fluids and optionally preservatives. The term paints covers, for example, physically or oxidatively drying finishes, baking finishes, reactive finishes, two-component finishes, emulsion paints for weather-resistant coatings and distempers. Printing inks are to be understood as those for printing on paper, textiles and sheet metal. Pigments obtained according to the invention are particularly suitable for paints and for use in automotive finishes, especially for metal-effect finishes. They show excellent fastness to water and solvents, to overpainting and overspraying, to sublimation and, in particular, have excellent fastness to light and weathering. With high brilliance, their nuance is markedly more red than that of the bromine-free compounds.

EXAMPLES

EXAMPLE 1

(a) 17.5 g of 2,5-dihydroxy-p-benzoquinone and 56.0 g of 3-amino-9-ethylcarbazole are heated under reflux for 2 hours in a mixture of 530 ml of glacial acetic acid and 25 ml of 10% strength sulphuric acid. After cooling, the batch is filtered hot with suction, and the residue is washed with 400 ml of glacial acetic acid and then with 2 l of hot water and dried at 100° C. This gives 60.0 g of the compound of the formula

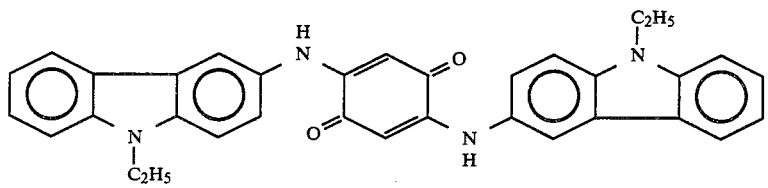

(b) 20.0 g of the above compound are heated to 190° C. in 1 l of nitrobenzene. 22 ml of bromine are quickly added dropwise. The mixture is stirred for a further 30 minutes at 190° C., hydrogen bromide being removed at the end by passing air over the mixture. After hot filtration with suction, the residue is washed with nitrobenzene until the run-off is colourless, then washed with methanol and dried at 100° C. This gives 31.6 g of a dioxazine having a bromine content of 50.3%. The compound thus corresponds to the following formula

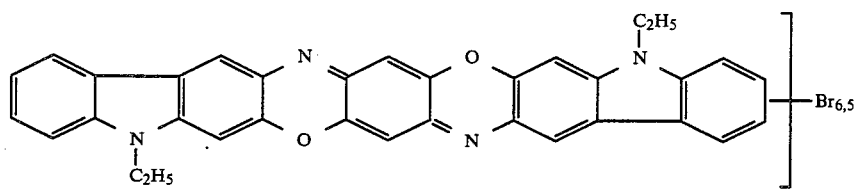

EXAMPLE 2

56.0 g of the compound

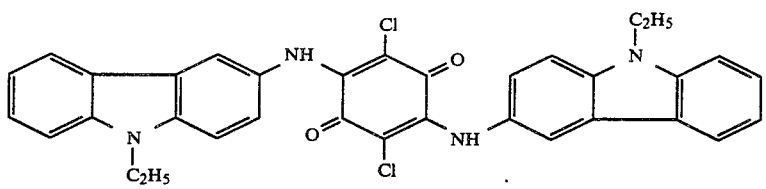

known as a precursor for C.I. Pigment Violet 23 are reacted according to Example 1b in 2 l of boiling nitrobenzene with 50 ml of bromine. This gives 82.1 g of a dioxazine having a bromine content of 51.6% and a residual chlorine content of 0.3%.

EXAMPLE 3

6.6 g of anhydrous sodium acetate are added to a mixture of 17.5 g of 3-amino-9-ethylcarbazole and 9.8 g of chloranil in 200 ml of nitrobenzene, and the mixture is stirred for 1 hour without heating. After heating to 180° C., 15.5 ml of bromine are added dropwise and stirring is continued for 40 minutes at 180° C., an air stream being finally passed over the mixture in order to remove hydrogen bromide. After hot filtration with suction, the residue is washed with nitrobenzene, then with methanol and finally with water and is dried at up to 120° C. The dioxazine thus obtained has a bromine content of 52.7% and a chlorine fraction of 2.5%. The compound thus corresponds to the following formula

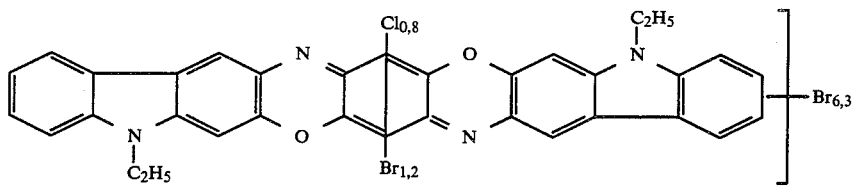

I claim:
1. A process for the preparation of a dioxazine compound of the formula

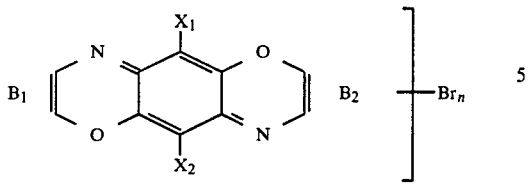

in which
B₁ and B₂ designate a ring system with 1, 2, 3 or 4 carbocyclic and/or heterocyclic rings which can be substituted, and
X₁ and X₂ designate hydrogen, halogen, —R′, —OR′, —NHR′, —NR′R″, $$-NH-\underset{\underset{O}{\|}}{C}R', \quad -\underset{\underset{O}{\|}}{N}-\underset{R''}{\overset{|}{C}}R', \quad -O-\underset{\underset{O}{\|}}{C}R', \quad -\underset{\underset{O}{\|}}{C}-NH_2, \quad -\underset{\underset{O}{\|}}{C}-NHR',$$

$$-\underset{\underset{O}{\|}}{C}-NR'R'', \quad -\underset{\underset{O}{\|}}{C}-OR',$$

R′ and R″ representing alkyl, cycloalkyl, aryl and aralkyl and
n denoting 2, 3, 4, 5, 6, 7, 8, 9, 10 or 11, it being possible for the n bromine atoms, independently of one another, to replace both H atoms of the ring systems B₁ and B₂ or their substituents and H atoms of X₁ and X₂ as well as X₁ and X₂ themselves, wherein a compound of the formula

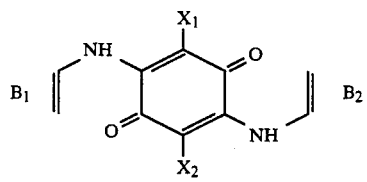

is reacted with bromine.

2. A process according to claim 1 for the preparation of a compound, in which B₁ and B₂ designate ring systems of the formulae

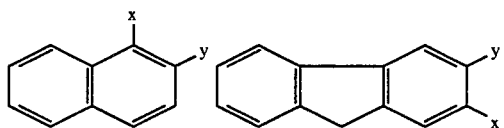

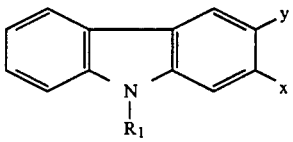

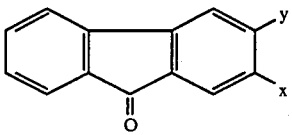

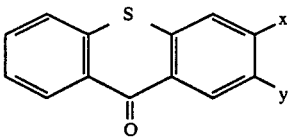

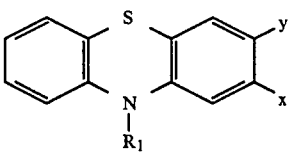

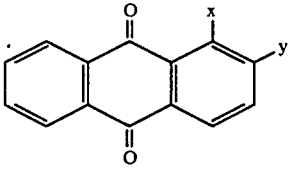

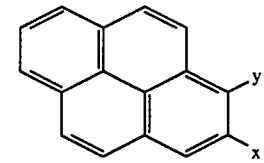

in which
R₁ represents hydrogen, R₂—, R₂—O—R₃—, $$R_2C-\underset{\underset{O}{\|}}{}$$

and R₂—SO₂—,
R₂ and R₃ designating alkyl, cycloalkyl, aralkyl or aryl and
the positions marked x indicating the bond with oxygen formed on cyclization and the positions marked y indicating the bond with the nitrogen.

3. A process according to claim 1 for the preparation of a compound of the formula

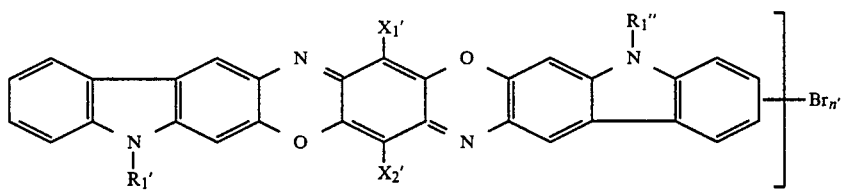

in which $X_1'$ and $X_2'$ have the same meanings as $X_1$ and $X_2$, and $R_1'$ and $R_1''$ represent hydrogen, $R_2$—, $R_2$—O—$R_3$—,

and $R_2$—SO$_2$—, $R_2$ and $R_3$ designating alkyl, cycloalkyl, aralkyl or aryl and n' designates 4, 5, 6, 7 or 8.

4. A process according to claim 3 for the preparation of a compound in which $X_1'=X_2'$ and/or $R_1'=R_1''$.

5. A process according to claim 3 for the preparation of compounds in which $X_1'$ and $X_2'$ are each H or Cl and $R_1'$ and $R_1''$ are $C_1$-$C_4$-alkyl.

6. A process according to claim 1 for the preparation of a compound of the formula

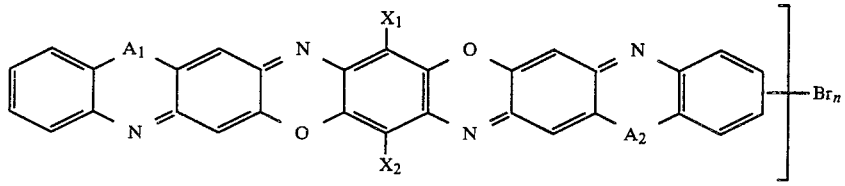

in which
$A_1$ and $A_2$ designate O, S or NR$_1$
wherein
$R_1$ represents hydrogen, $R_2$—, $R_2$—O—$R_3$—,

and $R_2$—SO$_2$—,
$R_2$ and $R_3$ designating alkyl, cycloalkyl, aralkyl or aryl,
wherein a compound of the formula

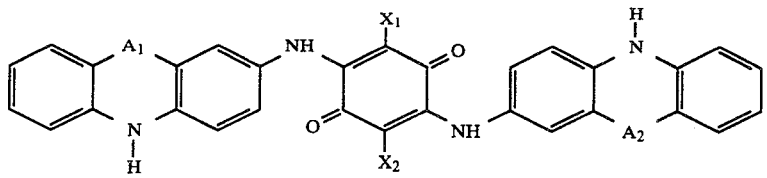

is reacted with bromine.

7. A process according to claim 1, wherein said process is carried out in the presence of a high-boiling solvent which is inert under the reaction conditions.

8. A process according to claim 1, wherein said process is carried out at 130°–250° C.

9. A process according to claim 1, wherein said process is carried out at 170°–220° C.

10. A process according to claim 1, wherein said process is carried out under pressure.

11. Process according to claim 4 for the preparation of a compound in which $X_1'$ and $X_2'$ are each H or Cl and $R_1'$ and $R_1''$ are $C_1$-$C_4$-alkyl.

12. A process according to claim 1, where said process is carried out in the presence of a diluent.

13. A process according to claim 5 where $R_1'$ and $R_1''$ are ethyl.

* * * * *

UNITED STATES PATENT AND TRADEMARK OFFICE
CERTIFICATE OF CORRECTION

PATENT NO. : 4,628,086

DATED : December 9, 1986

INVENTOR(S) : Günter Franke

It is certified that error appears in the above-identified patent and that said Letters Patent is hereby corrected as shown below:

Abstract, line 3 and 3rd line from bottom; Col. 1, line 10; Col. 1, line 40, Col. 1, line 63; Col. 4, line 5; Col. 4, line 15; Col. 9, lines 5 and 37

Place rings around "$B_1$" and "$B_2$" as follows:

-- $(B_1)$ -- ;

-- $(B_2)$ --

Signed and Sealed this

Fifteenth Day of March, 1988

Attest:

DONALD J. QUIGG

Attesting Officer

Commissioner of Patents and Trademarks